US005789230A

United States Patent [19]
Cotten et al.

[11] Patent Number: 5,789,230
[45] Date of Patent: Aug. 4, 1998

[54] ENDOSOMOLYTICALLY ACTIVE PARTICLES

[75] Inventors: Matthew Cotten; Susanna Chiocca; Gotthold Schaffner, all of Vienna; Ernst Wagner, Langenzersdorf, all of Austria

[73] Assignee: Boehringer Ingelheim International GmbH, Ingelheim am Rhein, Germany

[21] Appl. No.: 628,665

[22] PCT Filed: Oct. 7, 1994

[86] PCT No.: PCT/EP94/03313

§ 371 Date: Apr. 12, 1996

§ 102(e) Date: Apr. 12, 1996

[87] PCT Pub. No.: WO95/10624

PCT Pub. Date: Apr. 20, 1995

[30] Foreign Application Priority Data

Oct. 14, 1993 [DE] Germany .......................... 43 35 025.9

[51] Int. Cl.⁶ .............................. C12N 7/00; C12N 7/04; C12N 15/00; A61K 48/00

[52] U.S. Cl. .............. 435/235.1; 435/69.1; 435/172.3; 435/236; 435/320.1; 514/2; 514/44; 935/22; 935/52; 935/55

[58] Field of Search .................. 435/6, 320.1, 172.3, 435/252.3, 91.4, 69.1, 236; 536/23.5, 24.5; 424/93.6, 93.2; 935/22, 71, 52, 55; 514/44, 2

[56] References Cited

U.S. PATENT DOCUMENTS 5,635,383 6/1997 Wu et al. ......................... 435/172.3

Primary Examiner—Bruce R. Campell
Attorney, Agent, or Firm—Sterne, Kessler, Goldstein & Fox, PLLC

[57] ABSTRACT

Endosomolytically active virus-like particle which is made up of units of capsid proteins of viruses or virus-like particles, the capsid protein units having a membrane-active peptide sequence. The particles are suitable as components of compositions for transporting nucleic acids into higher eukaryotic cells by receptor-mediated endocytosis.

24 Claims, 4 Drawing Sheets

ENDOSOMOLYTICALLY ACTIVE PARTICLES

FIELD OF THE INVENTION

The invention relates to the introduction of nucleic acids into higher eukaryotic cells.

DESCRIPTION OF RELATED ART

In recent years the therapeutic use of gene therapy for treating numerous diseases has aroused interest. Gene therapy is used to synthesise in vivo therapeutically active gene products, by means of which, e.g. in the case of a genetic defect, the function of the defective gene is replaced. Examples of genetically caused diseases in which gene therapy constitutes a promising approach are haemophilia, beta-thalassaemia and "Severe Combined Immune Deficiency" (SCID), a syndrome caused by a genetically induced deficiency of the enzyme adenosine deaminase. Other possible uses are in immune regulation, in which humoral or intracellular immunity is achieved by means of vaccination. Other examples of genetic defects in which a nucleic acid coding for the defective gene can be administered, for example, in a form which is individually tailored to the particular requirements, include muscular dystrophy (dystrophine gene), cystic fibrosis ("Cystic fibrosis transmembrane conductance regulator gene") and hypercholesterolaemia (LDL receptor gene). Gene-therapeutic treatment methods may also be used in order to synthesise hormones, growth factors or proteins with a cytotoxic or immunomodulating activity in the body.

Gene therapy is also a promising approach to the treatment of cancer, involving the administration of so-called cancer vaccines. In order to increase the immunogenicity of tumour cells, these cells are altered either to make them more antigenic or to cause them to produce certain immunomodulating substances, e.g. cytokines which then trigger an immune response. In order to bring this about, the cells are transfected with DNA which codes for a cytokine, e.g. IL-2, IL-4, IFN-gamma or TNF-α. The most developed techniques for gene transfer into autologous tumour cells make use of viral vectors.

Nucleic acids as therapeutically active substances are also used for inhibiting certain cell functions, e.g. antisense RNAs and -DNAs or ribozymes have proved to be effective agents for selectively inhibiting certain gene sequences.

In recent times, gene transfer systems have been developed which circumvent the restrictions of the retroviral and adenoviral vectors and exclude their safety risks which are based on the co-transfer of viable viral gene elements of the original virus. These gene transfer systems are based on mechanisms which the cell uses in order to transport macromolecules, e.g. by the extremely effective route of receptor-mediated endocytosis (Wu and Wu, 1987; EP-A1 0 388 758; WO 91/17773, WO 92/17210 and WO 92/19281). Using this method, which makes use of bifunctional molecular conjugates which have a DNA binding domain and a domain with specificity for a cell surface receptor, high gene transfer rates have been achieved.

Since gene transfer by physiological route, such as receptor mediated endocytosis using nucleic acid complexes, has major advantages (non-toxic mechanism of passage through the cell membrane; possibility of administration of biologically active nucleic acids on a repeated or continuous basis; possibility of cell-specific targeting; the ability to produce the conjugates in large amounts), there is a need to make this system more efficient.

When using gene transfer techniques based on the principle of receptor-mediated endocytosis, it became apparent that a limiting factor of the system is the breakdown of the genetic material in the cell after it has been released from the endosomes. A substantial improvement in the system was therefore achieved by a technique which exploits the ability of certain viruses and virus components to open up endosomes. By adding these endosomolytic agents a substantial increase was achieved in the expression rates of the genes imported into the cell (Wagner et al., 1991a and 1991b; Cotten et al., 1992; Wagner et al., 1992a and 1992b; Zatloukal et al., 1992; Cotten et al., 1993a and 1993b; Curiel et al. 1991; WO 93/07283 and WO 93/07282).

Proposed endosomolytic agents, apart from viruses or virus components, were synthetic peptides derived from viral, pH-dependent, membrane-active peptides such as, for example, the influenza A haemagglutinin fusion peptide. Synthetic transfection complexes containing either the influenza peptide (WO 93/07283, Wagner et al., 1992) or various peptides based on the GALA peptide (Subbarao et al., 1987; Parente et al., 1990; and WO 93/07283) illustrated the usefulness of these peptides.

The use of synthetic membrane-active peptides as endosomolytic agents is, however, limited. This could be because they are possibly not always available, in the randomly ordered chemically or ionically bound gene transfer-complexes, in a form which allows them to perform their function.

The randomly arranged conjugates of synthetic peptides and polylysine which were used for complexing and condensing the DNA molecules lack an ordered three-dimensional structuring of the endosomolytic function such as that exhibited by the adenovirus particle, which is extremely efficient in terms of its endosomolytic activity. The endosomolytic activity of the adenovirus particle is assumed to be located in the pentone base (Seth et al., 1984) which is present in a defined copy number at specific sites on the surface of the virus particle (Stewart et al., 1993). This organised arrangement might have a function in terms of the requirements for the construction of a virus particle, but it might also play a part in controlling the interactions of the membrane-active motif on the pentone proteins with the endosome membrane.

SUMMARY OF THE INVENTION

The aim of the present invention was to provide endosomolytic agents which make it possible to improve the gene transfer systems using receptor-mediated endocytosis by ensuring high expression rates while substantially eliminating safety risks.

DESCRIPTION OF THE PREFERRED EMBODIMENTS

In setting out to solve this problem the primary consideration was to achieve improvements in the endosomolytic properties of the membrane-active peptides known from the prior art by combining them or arranging them in an ordered form, by placing them on a protein which is capable of assembling itself into particles having ordered structures.

In the course of carrying out the present invention, first the empty capsids, as found in normal adenovirus infections, were tested (Daniell, 1976). It was found that empty adenovirus capsids have no endosomolytic properties; these would appear to be activated later by proteolytic processing, which occurs at a late stage of virus maturation (Weber, 1976). This assumption accords with the fact that an adenovirus strain which is temperature-sensitive in terms of processing (Ad2 ts1; Weber, 1976) produces immature particles at the restrictive temperature and these particles are incapable of triggering the release of co-endocytosed material (Defer et al., 1990). In preliminary experiments relating to the present invention it was also found that these particles do not have the ability to improve DNA transportation or to break open liposomes. If this feature observed in adenoviruses is a general characteristic of virus maturation, it can be expected that empty capsids do not have the endosomolytic activity of the whole mature virus particles.

The present invention relates to an endosomolytically active virus-like particle which is made up of units of capsid proteins derived from capsid proteins of viruses or virus-like particles, the capsid protein units being modified with a membrane-active peptide sequence.

The framework of the particles according to the invention is an empty virus capsid or a capsid-like particle from proteins of viruses or virus-like particles such as bacteriophages or yeast transposons. The proteins which form the capsid structure are termed capsid proteins for the purposes of the present invention. The membrane-active peptide sequence is arranged on the capsid protein units in such a way as to ensure that it is functionally available at the site of its activity, i.e. in the cell: the membrane-active peptide sequences are either located freely on the surface of the particles or are arranged in the surface structure in such a way that their release is triggered by events in the cell such as proteolysis, a change in pH or a change in the Redox potential. The membrane-active function of the peptides, which is determined inter alia by their accessibility, is expressed in their endosomolytic activity. This is reflected by the increase in gene transfer capacity and can be tested by gene transfer experiments.

Empty capsids of simple viruses without a coat are available from a number of viruses. The natural capsids generally consist of one to three proteins. The possibility of preparing capsid proteins in large quantities, e.g. in the Baculovirus system, and their ability to assemble themselves have made it possible to obtain virus-like particles with ordered structures similar to those of the native virus. In most cases the particles are free from nucleic acid. (Empty capsids which themselves have endosomolytic activity which improves the uptake and expression of DNA transported into the cell, may be used as they are without any further modification of the particle, as proposed in WO 93/07283. One example of this is the empty capsids of the Parvovirus B19 which may be obtained, for example, by Baculovirus expression.)

The particles according to the invention are derived from capsid structures which, in themselves, do not have the endosomolytic activity required to increase the efficiency of the gene transfer, or do not have this activity to a sufficient or desirable degree.

The starting particles which form the structure may be natural in origin and in this case they are obtained particularly from virus infections.

Preferably, the particles are prepared by the recombinant method in which the optionally modified capsid proteins are expressed and purified and, if they are not already present in an associated form, they are subsequently allowed to associate.

If unmodified capsid proteins are expressed, the particles obtained after their association, which form the structure, may subsequently be modified on their surface with the membrane-active peptides, e.g. chemically by coupling with synthetic membrane-active peptides. The coupling of the membrane-active peptide to the capsid structure may be carried out in a manner known per se for the coupling of peptides, e.g. by a chemical method, whilst if necessary the individual components are provided with linker substances before the coupling reaction. Coupling may be carried out, for example, by means of disulphide bridges which may be cleaved again under reducing conditions (e.g. in the case of coupling by means of succinimidyl pyridyl dithiopropionate; Jung et al., 1981).

If the capsid has suitable carbohydrate chains, it may be attached to the peptide via these carbohydrate chains. The method described in WO 92/19281 for preparing glycoprotein-polycation conjugates may be used for this.

Another method of preparing the particles according to the invention is by enzymatic coupling of the membrane-active peptide to the structural capsid using a transglutaminase. The procedure described in WO 93/07283 for coupling polylysine to adenovirus may be used. The precondition is that glutamines or lysines corresponding to proteins must be available, which can be reacted by the enzyme.

Preferably, the particles according to the invention are obtained by preparing the modified capsid proteins using recombinant methods.

Thus, in another aspect, the invention relates to a process for the preparation of endosomolytically active virus-like particles, in which a DNA coding for a capsid protein of viruses or virus-like particles and modified with a sequence coding for a membrane-active peptide, is expressed and the resulting capsid protein is allowed to associate into capsid structures if necessary.

The chimeric DNA which contains a sequence coding for the capsid protein and a sequence coding for the membrane-active peptide, is expressed, for example, in insect cells transformed with Baculoviruses, in yeast or in bacteria. The resulting capsid protein modified by a membrane-active peptide domain may, for example, be allowed to associate, after the over-expressed capsid protein monomers have been denatured, purified and the denaturing agent removed. Suitable denaturing agents include, in particular, urea or guanidine hydrochloride, optionally in the presence of mild detergents and/or reducing agents. Denaturing is not necessary when the modified capsid proteins are already arranging themselves into capsid structures in the host organism, as is obviously the case with yeast-Ty particles. In this case the host cells are mechanically opened up and the ready capsid particles are harvested.

There are no restrictions regarding the expression system, of which a large selection is available for routine use. Preferably, a system is used which allows expression of the modified capsid proteins in large amounts; generally, bacterial expression systems are preferred on account of their efficiency. One example of a bacterial expression system suitable for use within the scope of the present invention is the one described by Studier et al., 1990. An example of a suitable yeast expression system is the one described by Emr, 1990; Baculovirus systems, which have already variously been used for preparing capsid proteins, are also suitable (e.g. O'Reilly et al., 1992). Constitutive or inducible expression systems may be used. By the choice and possible modification of available expression systems it is possible to control the form in which the capsids are obtained, e.g. a reduction in the expression rate may render the denaturing and subsequent resolubilisation of the capsid proteins superfluous.

Recombinant production, in which modification of the capsid proteins takes place in the course of the expression of the correspondingly modified DNA has the advantage, over subsequent modification of capsids, that the position of the membrane-active domains on the protein and the ratio of capsid proteins to membrane-active peptides can be defined precisely.

In the recombinant preparation of the modified capsid proteins its should be borne in mind that the presence of the membrane-active peptide, does not affect the ability of the expressed capsid proteins to combine into ordered structures, either by its sequence or by its arrangement. This requirement also applies to the site in the capsid protein where the peptide is inserted. If the capsids consist of more than one protein, the proteins may be co-expressed; for example, in the case of two capsid proteins, by co-transformation of the host organism with two plasmids each of which carries a capsid protein sequence, or by transformation of the host with a doubly recombinant vector which carries both sequences, as has been demonstrated, for example, for the expression of the capsid of the Parvovirus B19 in insect cells by means of Baculoviruses (Brown et al., 1991).

The currently available capsids which may be used for the purposes of the present invention, the proteins of which are expressed in the Baculovirus system and which can assemble themselves into particles, include the adeno-associated virus, a Dependovirus (Ruffing et al., 1992); "Aleutian Mink Disease Virus", an autonomous Parvovirus (Christensen et al., 1993); Flock House Virus, a Nodovirus (Schneeman et al., 1993), Papilloma virus; Poliovirus (Urakawa et al., 1989); Norwalk Virus (Jiang et al., 1992) and Polyomavirus. Examples of other capsid proteins which can be modified by the introduction of foreign domains include the L-A particle from yeast (Icho and Wickner, 1989; Wickner, 1993), the bacteriophages Qβ, GA, SP and other phages of the Leviviridae family, and the bacteriophages phi×174 (Ackerman and DuBow, 1987).

The yeast Ty particle and the MS2 phage bring particularly good preconditions: Kingsman et al., 1991, showed that ordered yeast Ty particles are suitable for the immunogenic multivalent preparation of peptides and small proteins such as HIV gp120 epitopes, hepatitis B antigens, etc. This is possible because the main protein of the Ty particle, the product of the TyA gene, has the ability to assemble itself into isometric particles measuring 40 nm (Burns et al., 1992). Kingsman et al. identified a fragment of the protein which is sufficient for this self-assembly activity; peptide sequences which are attached to the carboxy terminus of this protein are exposed on the surface of the assembled particle. The MS2 virus has a 24 nm quasi-icosahedral capsid, consisting of 180 copies of the main coat protein (13 kd), a copy of the maturation protein (45 kd) and a 3569 nt RNA genome. MS2 was the first organism to have its complete genome sequenced (Fiers et al., 1976). The crystalline structure of this virus was clarified and exhibited an exposed β-hairpin loop on-the surface of each of the 180-capsomers (Valegard et al., 1990). The non-fixed structure of this loop and its exposure on the surface were exploited in order to form particles for antigen presentation, by inserting sections from 11 to 26 amino acids into this loop (Mastico et al., 1993). The MS2 capsid protein tolerates these insertions whilst retaining its ability to assemble itself into ordered capsid structures; the capsid protein can be denatured-in urea and after removal thereof it assembles itself into native virus-like structures (Mastico et al., 1993). This makes it possible to assemble capsids which have numerous peptide epitopes on their surface.

The requirements imposed on the particle in general are that it should have a size of less than 100 nm, preferably less than 50 nm in diameter in order to allow it to be absorbed by endocytosis, it should be free from superfluous, particularly infectious nucleic acid which has no function for gene transfer, and it should have the ability to have an endosomolytic activity imparted to it (in the form of membrane-active peptides or small proteins), either chemically or by genetic manipulation.

The following particular requirements are imposed on capsids which are to be prepared recombinantly: the capsid should have the simplest possible structure, preferably consisting of a maximum of three subunits. The subunits should either associate by themselves in the host organism in which they are expressed or, if they are present in an insoluble form after over-expression, they should be capable of being resolubilised and of assembling themselves into capsid structures. For simplicity's sake the capsid proteins used are those whose genes are available in cloned form, otherwise cloning has to be carried out first. With regard to the insertion site for inserting the membrane-active peptide sequence, preferably capsid structures are used the 3D structure (crystalline structure) of which has been clarified by X-ray structural analysis. The sequence area in the capsid protein in which the membrane-active peptide sequence is provided is generally subject to the requirement that it should have no function for the construction of the capsid structure or assembly or that its function is not affected by the insertion of a peptide structure. If the crystalline structure is available, this is used to determine the site for inserting the peptide domain: if the crystalline structure shows that the virus or virus-like particle has loops on its surface, such as the MS2 phage, for example, these loops, which are not necessary for forming the capsid structure, are preferably used for the modification. If the crystalline structure is unknown, an empirical approach can be adopted when determining the insertion site: it is possible to tell from the amino acid sequence whether certain areas may form the basis for the construction of structural elements such as α-helical or β-folded sheet structures. If information regarding deletions or artificial or natural mutations of virus proteins allow any conclusions to be drawn as to the existence of unconserved regions, the unconserved regions which are not needed for the structure, such as the loops of the MS2 phage, for example, may be used for the modification.

When selecting capsid structures and membrane-active peptides and determining the insertion site of the peptide sequence for constructing the particles according to the invention, the following procedure is followed, for example: the DNA sequence or sequences coding for the capsid protein or proteins is or are introduced into a vector under the control of suitable expression control sequences and expressed in a suitable host. In parallel, vectors are expressed in which the capsid protein sequence is modified with a sequence coding for a membrane-active peptide. If necessary, first the insertion site for the foreign sequence is varied in order to obtain the optimum site. During the processing of the expression products, the conditions for purifying the capsid monomers and for their association may be adjusted to the ideal.

Thereafter, in a series of transfection experiments in which a reporter gene is conveniently used as DNA, under otherwise identical transfection conditions, the ability of the unmodified capsids and the capsids modified with various membrane-active peptides, optionally inserted at various sites on the capsid protein, are tested for their ability to improve the transportation of reporter DNA into the cell.

Theoretically, all membrane-active peptides are suitable for preparing the particles according to the invention, provided that they satisfy the requirement of not affecting the assembly of the capsid structures and of imparting to the particle in the cell the endosomolytic-function which brings about an increase in gene transfer efficiency. Suitable membrane active peptides, which may either be coupled subsequently to the starting particles or whose coding DNA sequence may be used to prepare chimeric capsid protein DNA, include, for example, the peptides described by Subbarao et al., 1987; Parente et al., 1990 and Wagner et al., 1992, as well as the natural and synthetic membrane-active endosomolytically active peptides described in WO 93/07283.

The suitability of yeast Ty particles to present foreign peptides on the surface has been exploited within the scope of the present invention in order to obtain genetically modified particles with membrane-active peptides on their surface, starting from yeast-Ty elements (Boeke et al., 1988).

Thus, in a preferred aspect, the invention relates to a yeast Ty particle made up of TyA protein units modified with a membrane-active peptide sequence.

In a preferred embodiment the Ty particle is modified with the peptide sequence (SEQ ID NO:8) Glu Ala Ala Leu Ala Glu Ala Leu Ala Glu Ala Leu Ala Glu His Leu Ala Glu Ala Leu Ala Glu Ala Leu Glu Ala Leu Ala Ala (GALA), which is located at the carboxy terminus of the TyA protein.

In another preferred embodiment the Ty particle is modified with the peptide sequence (SEQ ID NO:11) Gly Leu Phe Glu Ala Ile Glu Gly Phe Ile Glu Asn Gly Trp Glu Gly Leu Ala Glu Ala Leu Ala Glu Ala Leu Glu Ala Leu Ala Ala Gly Gly Ser, which is located on the carboxy-terminus of the TyA protein.

The yeast Ty particles according to the invention are obtained by expressing a DNA, coding for the TyA protein which has a membrane-active peptide sequence at the carboxy terminus, opening up the host cells and harvesting the capsids. Expression of the modified TyA sequence, e.g. in yeast or bacteria, yields modified Ty particles which can be purified on the basis of their size and density.

The purified endosomolytic Ty particles were biotinylated within the scope of the present invention and combined with streptavidine-polylysine and transferrin-polylysine as well as the DNA to be transported into the cell, in order to form ternary transfection complexes.

Alternatively, the endosomolytic Ty particles were coupled directly with polylysine using transglutaminase and combined with transferrin polylysine conjugates and the DNA to form ternary transfection complexes.

Moreover, within the scope of the invention, the tolerance of the MS2 phage for the insertion of foreign sequences into the loop located between the β-fold sheets near the N-terminus of the MS2 capsid protein was exploited, in that its capsid proteins were modified so as to express membrane-active peptide sequences on their surface.

Thus, another preferred embodiment of the present invention consists of an MS2 particle made up of MS2 capsid protein units modified with a membrane-active peptide sequence.

Preferably, the membrane-active peptide is inserted in the β-hairpin loop region between amino acid 11 (Asp) and amino acid 17 (Asp), particularly between amino acid 14 (Gly) and 15 (Thr) of the MS2 capsid protein. Another possible insertion site for the membrane-active peptide is in the C-terminal region of the MS2 capsid protein.

In a preferred embodiment of the invention the endosomolytic MS2 particle is modified with the peptide sequence GALA (SEQ ID NO: 8), which is inserted between amino acid 14 and amino acid 15 of the MS2 capsid protein.

The MS2 particles according to the invention are preferably obtained by expressing the capsid protein DNA, modified by the insertion of the sequence coding for the membrane-active peptide, then denaturing the resulting modified capsid protein and leaving it to associate, whilst removing the denaturing agent.

The purified endosomolytic MS2 particles were biotinylated within the scope of the present invention and combined with streptavidine polylysine and transferrin polylysine as well as the DNA to be transported into the cell in order to form complexes.

In a preferred embodiment, the particles according to the invention have, in addition to the membrane-active peptide or peptides, a peptide sequence with the function of a ligand for the target cell. In this way, an internalising function is imparted to the particle according to the invention, in addition to its endosomolytic function; this peptide sequence is hereinafter referred to as a "ligand peptide".

The best characterised ligand peptide is the arginine-glycine-aspartic acid sequence (RGD) which was found in various integrin-binding cell adhesion proteins such as fibronectin, fibrinogen, von Willebrand Faktor and Vitronektin (Pierschbacher und Ruoslahti, 1984; 1987). An RGD motif which is present in the pentone base of adenovirus type 2 and type 5 was shown to play a part in the internalising of the virus (Wickham et al., 1993). A synthetic version of the RGD sequence, containing a disulphide bridge and having a fixed structure, using the motif Cys-(Xaa)$_6$-Cys— in which the six amino acids contain in addition to the RGD sequence three other amino acids corresponding to the rules defined by Pierschbacher and Ruoslahti, 1987 and O'Neil et al., 1992—was found to have an affinity for an integrin substrate which was three orders of magnitude higher than a non-fixed version of the sequence (O'Neil et al., 1992). A sequence coding for this motif was also introduced into the M13 gene III in order to present it on the surface of the filamentary phage.

Such a short ligand peptide sequence containing the RGD motif can be introduced into capsid proteins in order to obtain particles according to the invention which have a cell-binding motif on their surface.

The ability, for example, of the MS2 capsid protein to assemble itself from urea-denatured monomers can also be used to produce MS2 particles having more than one foreign domain. The prerequisite for this is, once again, that these insertions should not interfere with the ability of the particles to assemble themselves. In order to obtain a particle according to the invention which has on the one hand a membrane-active domain (e.g. the GALA motif) and on the other hand a cell binding domain (e.g. the RGD motif) the procedure adopted is preferably to prepare on the one hand capsid monomers with a membrane-active modification and on the other hand those with a ligand modification, and to mix the two differently modified denatured monomers in a defined ratio and remove the denaturing agent in order to allow the modified proteins to combine to form virus-like particles.

As an alternative to the RGD motif, other ligand peptides may be inserted into the capsid monomers; examples include small peptide growth factors and hormones such as EGF (Epidermal Growth Factor) peptide, insulin, the co-stimulatory molecule HSA "Heat Stable Antigen" (Kay et al., 1990) as well as peptides of so-called superantigens coded by the murine mammary tumour virus (Torres et al., 1993).

In a preferred embodiment the particles according to the invention are provided with a nucleic acid-binding domain, particularly an organic polycationic compound such as polylysine. Other organic polycations, such as those proposed in WO 93/07283, for example, may be used as substances with an affinity for nucleic acid.

In this embodiment of the present invention, the virus-like particles thus contain in addition to the membrane-active endosomolytic peptides and optionally the cell binding ligand motifs, domains which are capable of binding to nucleic acids.

These particles which contain a DNA binding domain may be produced by subsequently conjugating the capsid with a DNA binding substance such as polylysine.

Conjugation of the capsid, e.g. with polylysine, may be carried out using the method known per se for coupling peptides to polyamine compounds, e.g. chemically, by coupling via a biotin-streptavidine bridge or by directly binding the polylysine to the capsid using transglutaminase. A similar procedure may be used to that described in WO 93/07283 for coupling polylysine to viruses or virus components.

As an alternative to subsequent conjugation of capsids with a DNA-binding peptide, modification of the capsid proteins with a DNA binding domain may also be carried out directly, i.e. by expression of a chimeric DNA sequence consisting of a DNA sequence coding for the capsid protein, and a sequence coding for the DNA-binding peptide.

In this method of production, the DNA-binding peptide is subject to the requirement which applies to the other foreign domains, namely that its presence on the capsid protein should not affect the ability of the capsid protein to assemble into ordered structures.

Examples of DNA-binding motifs which are present after expression of the chimeric capsid DNA on the particles according to the invention include cationic polypeptides, e.g. the homologs polylysine, polyarginine, or peptides, derived from naturally occurring DNA-binding proteins such as histones, core-proteins of adenovirus (e.g. protein V, protein VII and the 13 kd protein L211K) or protamines.

The presence of a polycationic domain in the form of polylysine enables complex forming of the capsid conjugates according to the invention with the nucleic acid to be transported into the cell.

The preparation of particles according to the invention which have more than one foreign domain, e.g. several membrane active domains or one membrane active domain in conjunction with one ligand-binding domain and/or one DNA binding domain, may be carried out in two or more separate, identical or different expression systems.

Thus, for example, a capsid protein monomer may be prepared with a membrane active domain, e.g. the peptide GALA, on the one hand and a capsid monomer with a ligand domain, e.g. the RGD motif, on the other hand and the monomers are mixed together in the desired ratio so as to assemble themselves into ordered structures. The optimum mixing ratio is determined empirically.

The particles according to the invention are used as endosomolytic agents in compositions for gene transfer, as described in WO 93/07283.

Thus, in another aspect, the invention relates to a composition for transporting nucleic acid into the higher eukaryotic cell, in which the nucleic acid is complexed with endosomolytically active virus-like particles, consisting of modified units of capsid proteins, derived from viruses or virus-like particles, in which the capsid protein units have membrane active peptide sequences and polycationic sequences for binding the nucleic acid.

In a preferred embodiment the gene transfer complexes contain, in addition to the endosomolytic particles according to the invention which have a nucleic acid binding domain, a conjugate in which a nucleic acid binding domain, generally the same as that of the particle, is coupled with an internalising factor for the target cell which is to be transfected. These ternary complexes or combined complexes are used particularly when the endosomolytic particle cannot on its own penetrate into the target cell, i.e. when it cannot penetrate into the cell in its native form and has not been modified with a ligand domain for the target cell either. However, this embodiment can also be used when the ligand function of a particle according to the invention is to be supplemented by an additional ligand function.

The preferred transfection complexes according to the present invention are those consisting of DNA, the particle conjugated with polylysine according to the invention and a transferrin-polylysine conjugate.

The transfection complexes may additionally contain a nucleic acid binding substance, especially polylysine, in a non-conjugated form, in order to condense the nucleic acid. In this case, the nucleic acid binding domain contained in the particle according to the invention or in the internalising factor conjugate has the function of adhering to the nucleic acid without saturating all the negative charges.

For a definition of the term "internalising fator" and the use of internalising factor conjugates together with the endosomolytic particles according to the invention in ternary transfection complexes, reference is made to the disclosure of WO 93/07283.

EXAMPLES

Figure 1:
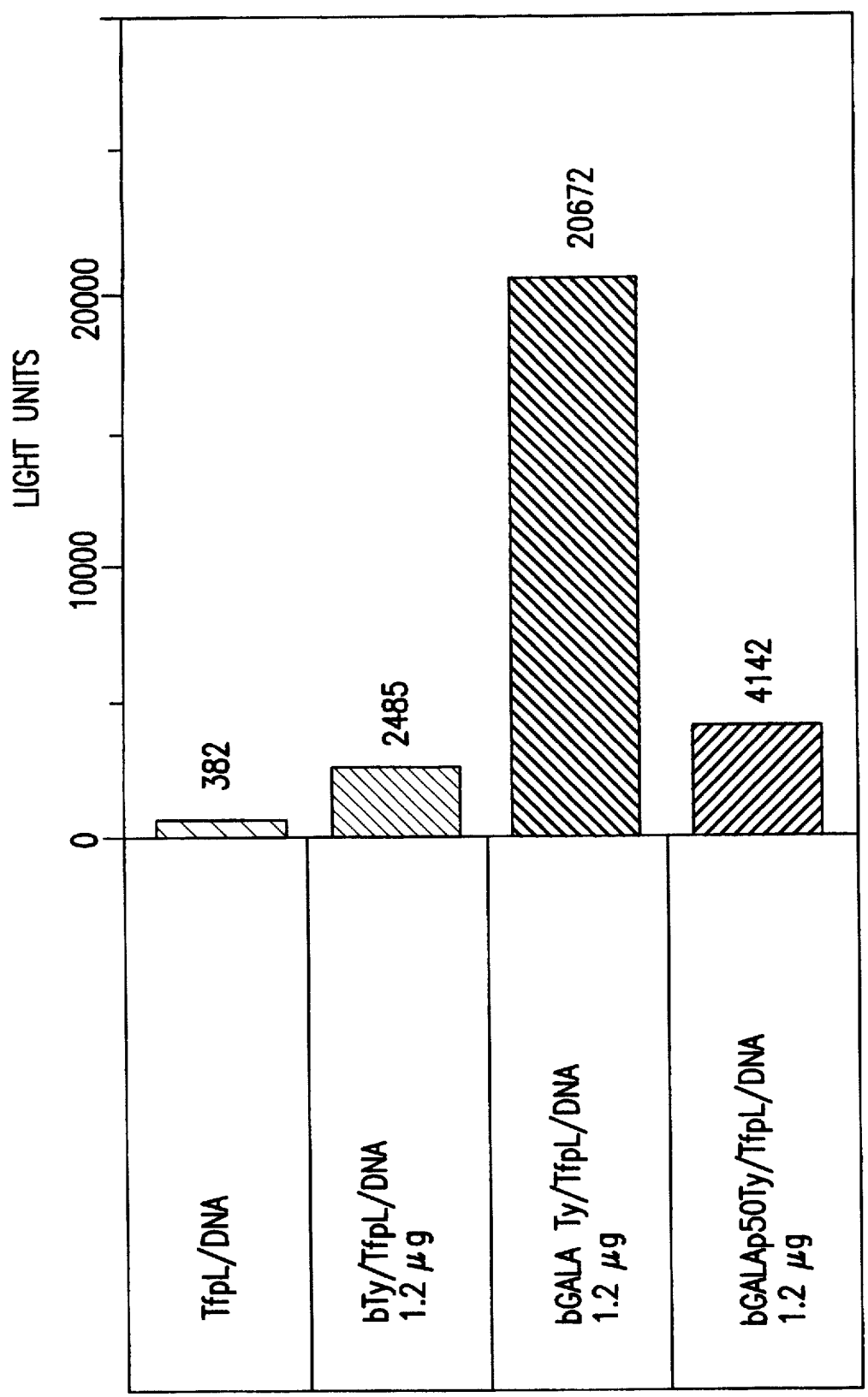
FIG. 1: Transfer of DNA into K562 cells by means of transfection complexes, containing endosomolytic Ty particles coupled to polylysine by means of biotin-streptavidine

The invention is illustrated by means of the following Examples:

Example 1 a) Construction of the Ty expression plasmid

The plasmid pJef1668 was used as the starting plasmid. This plasmid is derived from the plasmid pGTyH3 described by Boeke et al., 1988, from which the two internal Bgl II fragments have been removed. First of all the BamHI site at position 2695 was removed by cutting with BamHI, filling with Klenow and religating; the resulting clone was named pJefnoBam. The PCR primer designated TyBstX.1 (SEQ ID NO:1) and Tya.2 (SEQ ID NO:2) was used with pJef1668 as the starter to form an 870 bp fragment (fragment 1) which contains a new BamHI site at position 1952. Then pJefnoBam was used as starter in order to obtain the fragment 2 with the primers designated TyB.1 (SEQ ID NO:3) and TyB.2 (SEQ ID NO:4). The SalI/BstXI fragment from pJef1668 was removed and replaced by the PCR fragments 1 and 2. Then a synthetic translation termination sequence was introduced into the BamHI site with the complementary oligonucleotides Tystop.1 (SEQ ID NO:5) and Tystop.2 (SEQ ID NO:6) in order to obtain the plasmid designated pJefTerm4.

This made it possible to insert DNA sequences coding for membrane-active peptides, which were to be expressed on the surface of the resulting TyA fusion protein, into the BamHI site which now occurs only once. Two different sequences coding for membrane-active peptides were inserted in this site: the complementary oligonucleotides designated GALA.1 (SEQ ID NO:7) and GALA.2 (SEQ ID NO:9), coding for the original GALA sequence minus Trp at the N-terminus (Subbarao et al., 1987; Parente et al., 1990) (SEQ ID NO:8); the complementary oligonucleotides GALAP50.1 (SEQ ID NO:10) and GALAP50.2 (SEQ ID NO:12) which code for the chimeric peptide designated GALAP50 (SEQ ID NO:11). The plasmids obtained were designated pJefGALA and pJefGALAP50; the plasmids were sequenced by means of the inserted region in order to confirm that the modification was correct.

b) Expression of modified Ty particles in yeast

The plasmids were inserted using the lithium acetate method (Schiestl and Gietz, 1989) into the pep *Saccharomyces cerevisiae* strain 1268, thereby transforming the latter to a uracil auxotrophy (the plasmid has a ura marker). Individual clones were selected on uracil-minus plates (per litre: 8 g of yeast/nitrogen base, without amino acids, 22 g agar, 55 mg tyrosine, 55 mg of adenine and 11 g of CAA vitamin assay were autoclaved, cooled to 50° C., 100 ml. of 10% raffinose, 10 ml of 0.5% tryptophan and 10 ml of 0.5% leucine were added) and expanded in uracil minus medium (identical to the composition on the plates but without agar). After 24 hours growth at 30° C. (cell density about $10^8$ cells per ml) galactose was added (to 2%) in order to induce the gal4 promoter and the cells were allowed to grow for another 24 hours. Then the induced cells were harvested by centrifuging, washed in water and finally taken up in 4 ml of cold buffer B/Mg (10 mM HEPES-KOH pH 7.8, 15 mM KCl, 5 nM $MgCl_2$, 3 mM DTT, 10 μg/ml aprotinin) in 50 ml Falcon tubes. All the other steps were carried out on ice: the cells were lysed by the addition of 5 g of cold acid-washed glass beads and 5 minutes vortexing interrupted by 30 to 60 seconds cooling on ice. The suspension was centrifuged for 5 minutes at 3000 rpm (4° C.) and the supernatant was kept on ice (15 ml Corex tubes). This step was repeated twice more, with 4 ml and 3 ml of the same buffer. The lysate was finally centrifuged for 10 minutes at 10,000 rpm (4° C.) in a Sorvall SS34 rotor. Batches (2.75 ml) of the homogenised material were then transferred into 3 ml centrifuge tubes, then 250 μl of 60% saccharose in buffer B/EDTA (corresponding to buffer B/Mg without aprotinin and $MgCl_2$, containing 10 mM EDTA instead) were carefully layered underneath and centrifuged for 20 minutes at 100,000 rpm at 4° C. (TLA-100.3 rotor). The supernatant was discarded as far as the fuzzy intermediate phase above the saccharose cushion and the pellet was once again taken up in the residue remaining plus 1 ml of additional B/EDTA buffer, this material was placed in a fresh centrifuge tube and placed on 1.5 ml of 35% saccharose/B/EDTA buffer. For underlayering, 250 μl of the same material as in the first passage was used. Centrifuging was carried out exactly as on the first occasion; the material obtained in this way from repeated double centrifugation was combined, underlayered with 400 μl of 60% saccharose/B/EDTA buffer and centrifuged for 1 hour in an SW41 rotor at 4° C. and 39 rpm. The pellets obtained were taken up in about 1.5 ml of B/EDTA buffer, thereby diluting the saccharose to less than 12.5%, and subsequently the 800 μl samples of material were fractionated on a linear 15 to 50% saccharose gradient (13 ml) in B/EDTA buffer (25,000 rpm, 3 hours, 4° C., SW41 rotor). The fractions were investigated for their protein content by SDS/PAGE and the fractions containing the TyA protein were combined.

c) Modification of the Ty particles i) Biotinylation

The biotinylation of the Ty particles for the purpose of binding to streptavidine-polylysine was carried out essentially as described in WO 93/07283, inter alia, for adenovirus, by dissolving NHS-LC biotin (Pierce Cat.No. 21335) in 10 mM HEPES pH 7.9 to 1 mM and adding the biotin solution to the Ty particle solution (10 μl per ml). After 3 hours reaction at ambient temperature the sample was exhaustively dialysed against HBS/40% glycerol at 4° C. in order to remove any unreacted biotin.

ii) Coupling of polylysine by means of transglutaminase

As a result of the cloning method used to prepare the plasmid pJefGALA, the GALA sequence (SEQ ID NO:8) contains a lysine group; the addition of the biotin group and the subsequent binding of streptavidine could affect the membrane interaction expected of this sequence. Therefore, as an alternative, direct coupling of polylysine to the Ty particle was carried out using transglutaminase.

The reaction was carried out essentially as described in WO 93/07283: samples of the purified TyGALA particles (500 μl, 0.2 mg/ml) in 100 mM HEPES pH 7.9, 2 mM DTT, 10 mM $CaCl_2$, were incubated with 1 nmol of guinea-pig liver transglutaminase (Sigma) and 50 μl of polylysine (chain length 200; 1 mg/ml) for 2 hours at 37° C. The polylysine-modified Ty particles were cleansed of free polylysine by diluting the sample in HBS, underlayering it with a 60% saccharose cushion and centrifuging it for 40 minutes in a TLA-100.3 rotor. The centrifuged material was taken up in HBS/40% glycerol overnight at 4° C. and used directly for the DNA transfer experiments.

d) Preparation of human transferrin-polylysine

The method described by Wagner et al., 1991b, was used, in which polylysine is coupled to the carbohydrate side chains of transferrin.

A solution of 91 mg (1.14 μmol) of human transferrin (iron-free, Biotest Pharma) in 1.4 ml of 30 mM sodium acetate buffer, pH 5, was cooled to 0° C. and 34 μl of 30 mM sodium acetate buffer pH 5 containing 0.73 mg (3.4 μmol) of sodium periodate were added. The mixture was left to stand in the dark in an ice bath for 90 minutes. In order to remove the low molecular products, gel filtration was carried out (Sephadex G-25, Pharmacia) yielding a solution which contained about 82 mg (2 ml) of oxidised transferrin (measured by ninhydrin assay). (In order to detect the oxidised form which contains aldehydes and produces a colour reaction when stained with anisaldehyde, the samples were added dropwise to a silica gel thin layer plate, dried and the plates were immersed in p-anisaldehyde/sulphuric acid/ethanol (1/1/18), dried and heated.) The modified transferrin solution was quickly added (within 10 to 15 minutes) to a solution containing 1.0 μmol of poly(L)lysine with an average chain length of 250 lysine monomers in 0.9 ml of water. The pH of the solution was adjusted to pH 7.7 by the addition of 0.3 ml of 2M HEPES pH 7.9. At intervals of 1 hours, 4 batches of 8 mg (126.3 μmol) of sodium cyanoborohydride were added to the mixture. After 17 hours, 1 ml of 5M sodium chloride and 5.8 ml of water were added to bring the solution to a total concentration of about 0.5M. The reaction mixture was placed on a cation exchange column (Bio-Rad Macroprephigs in column HR 10/10) and fractionated with a saline gradient of 0.5M to 3.0M sodium chloride with a constant content of 20 mM HEPES pH 7.3. The high salt concentration on charging the column and from the start of the gradient was essential for obtaining the polycation conjugates. The majority of conjugates eluted at a salt concentration of between 2.1M and 2.6M and was pooled. After a single dialysis against 2 litres of HBS (20 mM HEPES pH 7.3 150 mM NaCl) these fractions yielded (in the order of elution) a main fraction (TfpL250) containing 54 mg (0.67 μmol) of transferrin modified wi th 39.4 mg=0.76 μmol of polylysine. If they were not used immediately, the transferrin conjugates were flash frozen and stored in liquid nitrogen at −20° C. in iron-free form. The incorporation of iron was carried out by adding 1.25 μl of 10 mM iron(III) citrate buffer (containing 200 mM citrate, adjusted to a pH of 7.8 by the a ddition of sodium bicarbonate) per mg of transferrin content. The conjugates containing iron, before being used for DNA complex formation, were divided up into small aliuots, flash frozen in liquid nitrogen or dry ice/ethanol and stored at −20° C. (This procedure proved useful once it was found that repeated thawing and freezing causes the conjugates to spoil.)

e) Gene transfer into K562 cells by means of transfection complexes which contain endosomolytic Ty particles i) Use of Ty particles conjugated with polylysine via biotin-streptavidine Transfection complexes containing biotinylated Wild type Ty-, TyGALA- or TyP50-particles were prepared as follows: the quantities of biotinylated Ty particles given in FIG. 1 were diluted in 150 μl of HBS and mixed with 150 μl of HBS containing 1 μg of streptavidine polylysine for 30 minutes at ambient temperature. Then a 100 μl aliquot of HBS containing 6 μg of pCMVL-DNA was added and the mixture was left to stand for 30 minutes at ambient temperature. Finally, a 100 μl aliquot of HBS containing 5.6 μg of transferrin polylysine was added. As a control, complexes of DNA, streptavidine polylysine and transferrin polylysine were used. These complexes were applied to 500,000 deferrioxamine-treated K562 cells as described in WO 93/07283. 24 hours later the cells were harvested, cell extracts were prepared and investigated for luciferase activity. It was found that the complexes used as controls did not function, that the Wild-type Ty particle brings about a slight increase in luciferase activity and that the content of biotinylated Ty which is modified with the membrane-active peptide GALA (SEQ ID NO:8) brings about an approximately 10-fold increase in DNA transfer in the complexes compared with the Wild type Ty particles. The Ty particles modifed with GALAP50 (SEQ ID NO:11) induced a slight increase in DNA transportation. (All the Figures show the averages from two transfections.)

ii) Use of Ty particles coupled directly to polylysine

Figure 2:
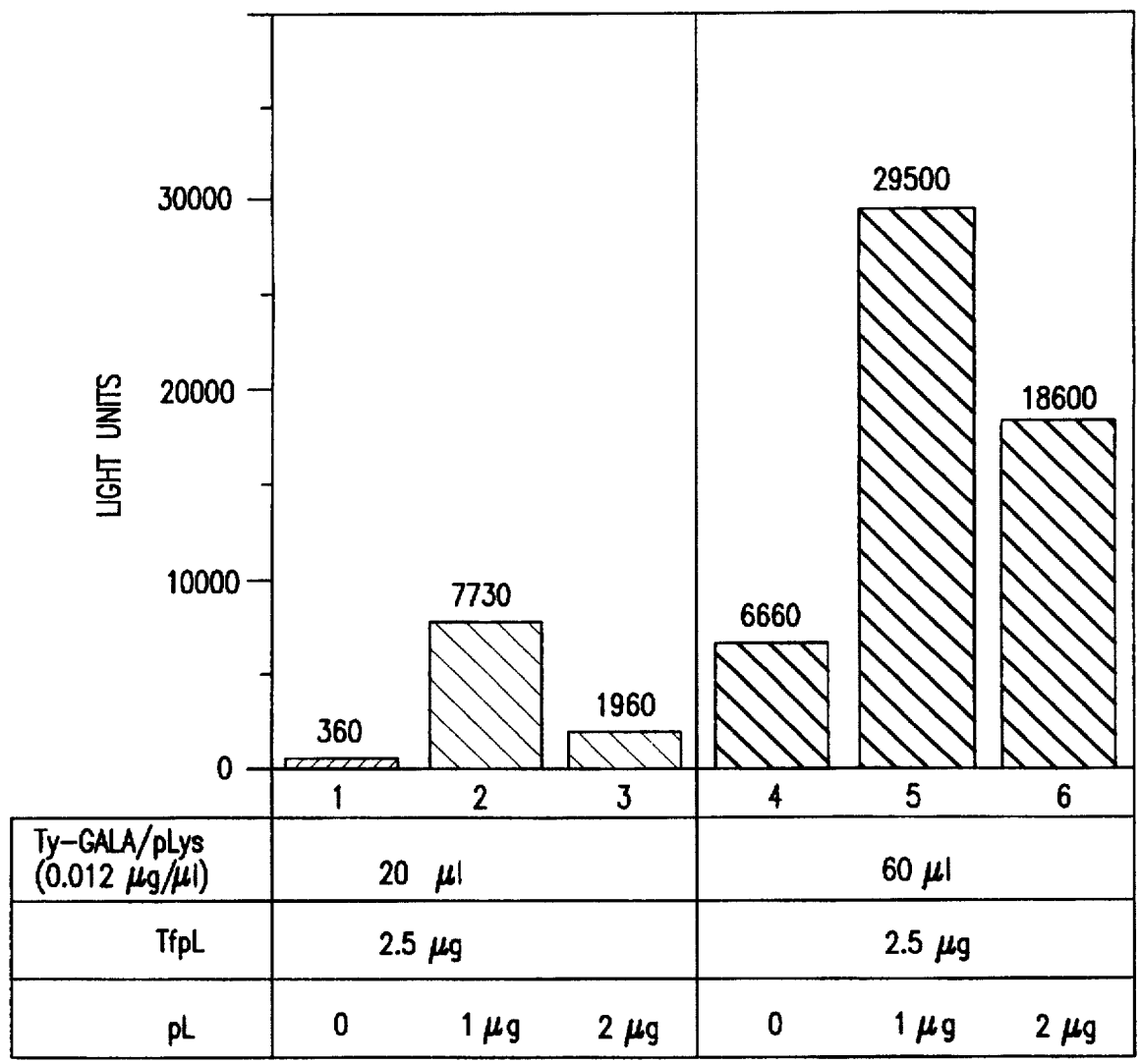
FIG. 2: Transfer of DNA into K562 cells by means of transfection complexes containing endosomolytic Ty particles coupled directly to polylysine

The polylysine-modified TyGALA particles were incorporated in DNA complexes as specified in i), except that there was no incubation with streptavidine/polylysine and the transferrin-polylysine/HBS solution additionally contained the quantities of free polylysine specified in FIG. 2 to ensure complete condensation of the DNA. The complexes were applied to deferrioxamine-stimulated cells, extracts were prepared 24 hours later and examined for luciferase activity. It was found that the absolute expression values achieved with the transglutaminase-coupled Ty-polylysine conjugates did not exceed those achieved with the biotin-streptavidine-coupled conjugates.

Example 2 a) Construction of MS2-capsid expression plasmids

The plasmid known as pPLaACR26 (Remaut et al., 1981) which contains the sequence coding for MS2 was obtained from the LMBP Culture Collection Laboratory of Molecular Biology at the University of Ghent in Belgium. In order to isolate the MS2 capsid sequence as a BglII fragment and to mutate the sequence in order to form a BamHI site which occurs only once in the nucleotides which code for amino acid 15, the PCR method was used. The PCR fragment was purified by gel electrophoresis and ligated into the BamHI-cut plasmid pETH2a (pETH2a is the T7 expression vector pET2a (Studier et al., 1990) in which the small NdeI/BamHI site has been replaced by the complementary oligonucleotides A (SEQ ID NO:13) and B (SEQ ID NO:15) coding for polyhistidine (SEQ ID NO:14). A clone designated pMS2WT9 which contained the insert in the correct orientation was isolated; the presence of the correct sequence was confirmed by sequencing.

The plasmid pMS2GALA4 was prepared by inserting the complementary oligonucleotides GALAMS1 and GALAMS2 coding for GALA into the single BamHI site of pMS2WT9. GALAMS1 is identical to GALA.1 (SEQ ID NO:7), except that T in position 5 has been removed. GALAMS2 is identical to GALA.2(SEQ ID NO:9), except that the terminal A has been removed. In this way the GALA sequence (SEQ ID NO:8) is placed in the correct reading frame for expression of the modified MS2 capsid. The presence of the correct DNA insert in the correct orientation was again confirmed by DNA sequencing.

b) Expression of MS2 capsids

The plasmids pMS2WT9 and pMS2GALA4 were transformed in the T7 expression bacteria strain BL21 (DE3) (Studier et al., 1990; obtained from Novagen), individual colonies were selected and grown in 1 litre cultures ($OD_{600}$= 0.7), then IPTG (to 1 mM) was added in order to induce T7 polymerase expression and subsequently expression of the MS2- and MS2GALA-proteins. After 4 hours at 37° C. the cells were harvested by centrifuging and the bacterial cell pellets were lysed in 6M guanidine hydrochloride, 0.1M sodium phosphate, 10 mM β-mercaptoethanol and 10 mM Tris, pH 8.0 (buffer A) whilst stirring for 1 hour at room temperature. The lysate was clarified by centrifuging at 17,000 rpm (Sorval SS34 Rotor) and the supernatant was passed over a 3 ml nickel chelate NTA sepharose column equilibrated with buffer A in order to harvest the polyhistidine-labelled proteins. The columns were eluted with 10 column volumes of buffer A; 5 column volumes of 6M urea, 100 mM sodium phosphate, 10 mM Tris, pH 6.5; 5 column volumes of 6M urea, 100 mM sodium phosphate, 10 mM Tris, pH 5.7. Finally, 5 column volumes of 0.2N acetic acid/6M guanidine hydrochloride were used to elute the MS2- and MS2GALA-proteins. In order to eliminate the denaturing agent the eluates were passed over small gel filtration columns (Pharmacia "Nick Columns" or Pharmacia PD-10 columns) equilibrated with 100 mM DTT, 40 mM HEPES, pH 7.4.

c) Biotinylation of MS2 capsids

Figure 3:
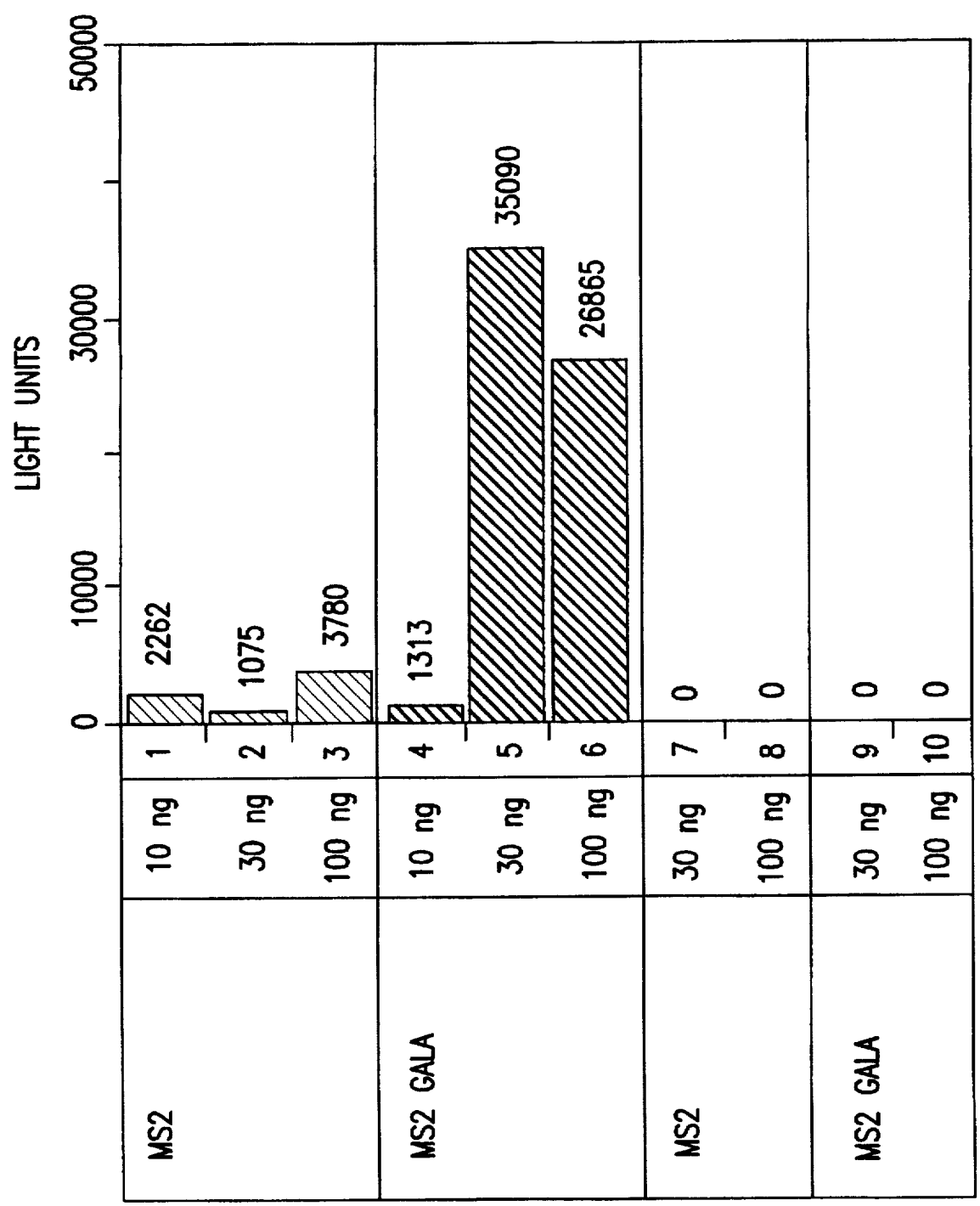
FIGS. 3 and 4: Transfer of DNA into K562 cells by means of transfection complexes containing endosomolytic MS2 particles coupled to polylysine via biotin-streptavidine
Figure 4:
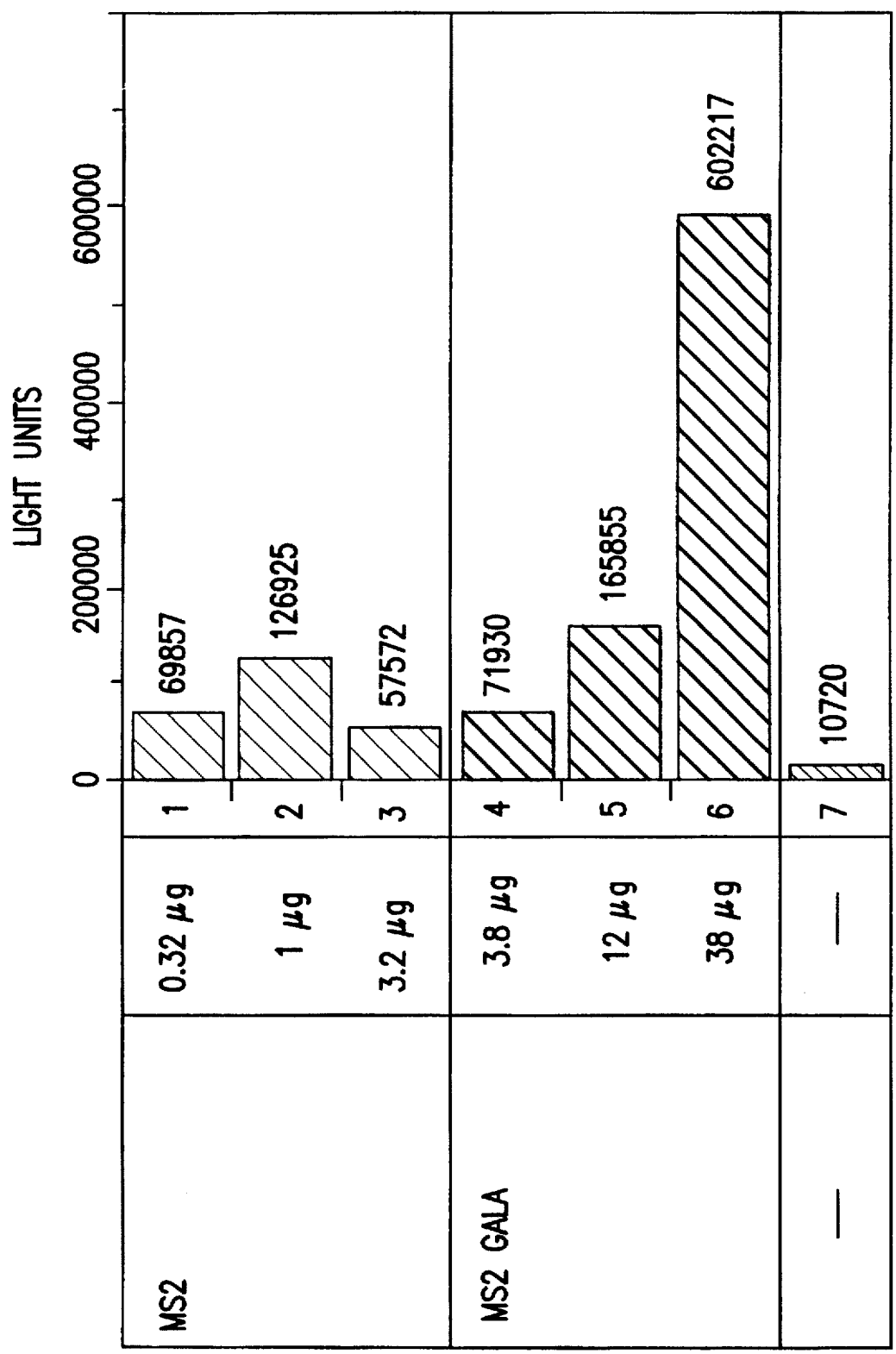

The capsid proteins obtained in b) were biotinylated in the same way as the Ty particles in the preceding Example, exhaustively dialysed against 40 mM HEPES pH 7.4 and stored at 4° C.

d) Gene transfer into K562 cells by means of transfection complexes containing endosomolytic MS2 particles i) Transfection complexes containing biotinylated MS2 particles were prepared as follows: the quantities of biotinylated MS2 particles specified in FIG. 3 (Wild type MS2 and MS2-GALA in biotinylated (samples 1–6) and unmodified (samples 7–9) form) were diluted in 150 μl of HBS and mixed with 150 μl of HBS containing 1 μg of streptavidine-polylysine for 30 minutes at ambient temperature. Then a 100 μl aliquot of HBS containing 6 μg of pCMVL-DNA was added and the mixture was left to stand for 30 minutes at ambient temperature. Finally, a 100 μl aliquot of HBS containing 5.6 μg of transferrin-polylysine (see Example 1) was added. These complexes were applied to 500,000 deferrioxamine-treated K562 cells as described in WO 93/07283. 24 hours later, the cells were harvested, cell extracts were prepared and examined for luciferase activity.

ii) A second test series was carried out with biotinylated Wild type MS2 and MS2-GALA, as in i), except that larger quantities (as in FIG. 4) of biotinylated MS2 particles were used. It was found that the biotinylated Wild type particles (samples 1–3) brought about only a small increase in DNA transportation compared with the background, whereas the presence of biotinylated MS2-GALA particles (samples 4–6) stimulated the DNA transportation corresponding to 600,000 light units. (Sample 7 contained MS2 particles.)

BIBLIOGRAPHY

Ackerman, H. W. and DuBow, M. S., 1987, Viruses of Prokaryotes, Vol. II, pp. 171–218, CRC Press, Boca Raton, Fla.

Boeke, J., Eichinger, D., Castrillon, D. and Fink, G., 1988, Mol. Cell. Biol. 8, 1432–1442.

Brown, C. S., van Lent, W. M., Vlak, J. M. and Spaan, W. J. M., 1991, J. Virol. 65, 2702–2706.

Burns, N., Saibil, H., White, N., Pardon, J., Timmons, R., Richardson, S., Richards, B., Adams, S., Kingsman, S. and Kingsman, A., 1992, EMBO J. 11, 1155–1164.

Christensen, J., Storgaard, T., Bloch, B., Alexandersen, S. and Aasted, B., 1993, J. Virol. 67, 229–238.

Cotten, M., Wagner, E., Zatloukal, K., Phillips, S., Curiel, D. and Birnstiel, M. L., 1992, Proc.Natl.Acad.Sci. USA 89, 6094–6098.

Cotten, M., Wagner, E. and Birnstiel, M. L., 1993a, Methods Enzymol. 217, 618–644.

Cotten, M., Wagner, E., Zatloukal, K. and Birnstiel, M. L., 1993b, J. Virol. 67, 3777–3785.

Curiel, D. T., Agarwal, S., Wagner, E. and Cotten, M., 1991, Proc.Natl.Acad.Sci. USA 88, 8850–8854.

Daniell, E., 1976, J. Virol. 19, 685–708.

Defer, C., Belin, M., Caillet-Boudin, M. and Boulanger, P., 1990, J. Virol. 64, 3661–3673.

Emr, S. D., 1990, Methods Enzymology 185, 231–233.

Fiers, W., Contreras, R., Duerinck, F., Haegeman, G., Iserentant, D., Merregaert, J., Minjou, W., Molemans, F., Raeymaekers, A., Van den Berghe, A., Volckaert, G. and Ysebaert, M., 1976, Nature 260, 500–507.

Icho, T. and Wickner, R. B., 1989, J. Biol. Chem. 264, 6716–6723.

Jiang, X., Wang, M., Graham, D. Y. and Estes, M. K., 1992, J. Virol. 66, 6527–6532.

Jung, et al., 1981, Biochem. Res. Commun. 101, 599.

Kay, R., Takei, F. and Humphries, R. K., 1990, J. Immunology 145, 1952–1959.

Kingsman, A. J., Adams, S. E., Burns, N. R. and Kingsman, S. M., 1991, Trends in Biotechnology 9, 303–309.

Mastico, R. A., Talbot, S. J. and Stockley, P. G., 1993, J. Gen. Virology 74, 541–548.

O'Neil, K. T., Hoess, R. H.; Jackson, S. A., Ramachandran, N. S., Mousa, S. A. and DeGrado, W. F., 1992, Proteins 14, 509–515.

O'Reilly, D. R., Miller, L. K. and Luckow, V. A., 1992, Baculovirus expression vectors. W. H. Freeman & Co. New York.

Parente, R. A., Nir, S. and Szoka, F. C., 1990, Biochemistry 29, 8720–8728.

Pierschbacher, M. D. and Ruoslahti, E., 1984, Nature 309, 30–33.

Pierschbacher, M. D. and Ruoslahti, E., 1987, J. Biol. Chem. 262, 17294–17298.

Remaut, E., Stanssens, P. and Fiers W., 1981, Gene 15, 81–93.

Ruffing, M., Zentgraf, H. and Kleinschmidt, J. A., 1992, J. Virol. 66, 6922–6930.

Schiestl, R. H. and Gietz, R. D., 1989, Current Genetics 16, 339–346.

Schneeman, A., Dasgupta, R., Johnson, J. E. and Rueckert, R. R., 1993, J. Virol. 67, 2756–2763.

Seth, P., FitzGerald, D., Ginsberg, H., Willingham, M. and Pastan, I., 1984, Mol. Cell. Biol. 4, 1528–1533.

Stewart, P. L., Fuller, S. D. and Burnett, R. M., 1993, EMBO J. 12, 2589–2599.

Studier, W., Rosenberg, A. H., Dunn, J. J. and Dubendorff, J. W., 1990, Methods Enzymol. 185, 60–89.

Subbarao, N. K., Parente, R. A., Szoka, F. C., Nadasdi, L. and Pongracz, K., 1987, J. Biol. Chem. 26, 2964–2972.

Torres, B. A., Griggs, N. D. and Johnson, H. M., 1993, Nature 364, 152–154.

Urakawa, T., Ferguson, M., Minor, P. D., Cooper, J., Sullivan, M., Almond, J. W. and Bishop, D. H. L., 1989, J. Gen. Virol. 70, 1453–1463.

Valegard, K., Lijas, L., Fridborg, K. and Unge, T., 1990, Nature 345, 36–41.

Wagner, E., Cotten, M., Foisner, R. and Birnstiel, M. L., 1991a, Proc.Natl.Acad.Sci. USA 88, 4255–4259.

Wagner, E., Cotten, M., Mechtler, K., Kirlappos, H. and Birnstiel, M. L., 1991b, Bioconjugate Chemistry 2, 226–231.

Wagner, E., Zatloukal, K., Cotten, M., Kirlappos, H., Mechtler, K., Curiel, D. and Birnstiel, M. L., 1992a, Proc.Natl.Acad.Sci. USA 89, 6099–6103.

Wagner, E., Plank, C., Zatloukal, K., Cotten, M. and Birnstiel, M. L., 1992b, Proc.Natl.Acad.Sci. USA 89, 7934–7938.

Weber, J., 1976, J. Virol. 17, 462–471.

Wickner, R. B., 1993, J. Biol. Chem. 268, 3797–3800.

Wickham, T. J., Mathias, P., Cheresh, D. A. and Nemerow, G. R., 1993, Cell 73, 309–319.

Wu, G. Y, and Wu, C. H., 1987, J. Biol. Chem. 262, 4429–4432.

Zatloukal, K., Wagner, E., Cotten, M., Phillips, St., Plank, C., Steinlein, P., Curiel, D. and Birnstiel, M. L., 1992, Annals New York Academy of Sciences 660, 136–153.

We claim:

1. A non-naturally occurring virus-like particle, which comprises units of capsid proteins modified with a membrane-active peptide sequence; wherein said capsid proteins are derived from viruses or virus-like particles; and wherein said non-naturally occurring virus-like particles are endosomolytically active.

2. A particle according to claim 1, wherein said particle is a modified yeast-Ty particle which is made up of units of TyA protein modified with a membrane-active peptide sequence.

3. A particle according to claim 2, wherein said Ty particle is modified with the peptide sequence Glu Ala Ala Leu Ala Glu Ala Leu Ala Glu Ala Leu Ala Glu His Leu Ala Glu Ala Leu Ala Glu Ala Leu Glu Ala Leu Ala Ala (SEQ ID NO: 8), which is located at the carboxy terminus of the TyA protein.

4. A particle according to claim 2, wherein said Ty particle is modified with the peptide sequence Gly Leu Phe Glu Ala Ile Glu Gly Phe Ile Glu Asn Gly Trp Glu Gly Leu Ala Glu Ala Leu Ala Glu Ala Leu Glu Ala Leu Ala Ala Gly Gly Ser (SEQ ID NO: 11), which is located at the carboxy terminus of the TyA protein.

5. A particle according to claim 1, wherein said particle is a modified MS2 particle which is made up of units of the MS2 capsid protein modified with a membrane-active peptide sequence.

6. A particle according to claim 5, wherein the membrane-active peptide is inserted in the β-hairpin loop region between amino acid 11 (Asp) and amino acid 17 (Asp) of the MS2 capsid protein.

7. A particle according to claim 6, wherein the membrane-active peptide is inserted in the β-hairpin loop region between amino acid 14 (Gly) and amino acid 15 (Thr) of the MS2 capsid protein.

8. A particle according to claim 5, wherein said particle is modified with the peptide sequence Glu Ala Ala Leu Ala Glu Ala Leu Ala Glu Ala Leu Ala Glu His Leu Ala Glu Ala Leu Ala Glu Ala Leu Glu Ala Leu Ala Ala (SEQ ID NO: 8).

9. A particle according to claim 1, wherein said particle also has a nucleic acid-binding domain.

10. A particle according to claim 9, wherein said nucleic acid-binding domain is polylysine.

11. A particle according to claim 10, wherein said particle is bound directly to polylysine.

12. A particle according to claim 1, wherein said particle also has a peptide sequence which has the function of a ligand for a higher eukaryotic cell.

13. A composition for transporting nucleic acid into a higher eukaryotic cell, which comprises an endosomolytic agent, wherein said endosomolytic agent is an endosomolytically active virus-like particle according to claim 8.

14. A composition according to claim 13, wherein said composition also contains a conjugate of a nucleic acid-binding substance and an internalizing factor for the cell.

15. A composition according to claim 14, wherein said composition contains a transferrin-polylysine conjugate.

16. A composition for transporting nucleic acid into a higher eukaryotic cell, which comprises an endosomolytic agent, wherein said endosomolytic agent is an endosomolytically active virus-like particle according to claim 12.

17. A composition according to claim 16, wherein said composition also contains a conjugate of a nucleic acid-binding substance and an internalizing factor for the cell.

18. A composition according to claim 17, wherein said composition contains a transferrin-polylysine conjugate.

19. A particle according to claim 1, wherein said viruses or virus-like particles are selected from the group consisting of Dependovirus, Parvovirus, Nodovirus, Papilloma virus, Poliovirus, Norwalk Virus, Polyomavirus and Leviviridae bacteriophages.

20. A particle according to claim 1, wherein said viruses or virus-like particles are selected from the group consisting of adeno-associated virus, Aleutian Mink Disease Virus, Flock House Virus, L-A yeast particles, Qβ bacteriophages, GA bacteriophages, SP bacteriophages and phi×174 bacteriophages.

21. A process for preparing the particle of claim 1, wherein said process comprises the steps:

(a) expressing a DNA coding for a capsid protein of viruses or virus-like particles which is modified with a sequence coding for a membrane-active peptide, thereby obtaining a capsid; and (b) harvesting the capsid of step (a).

22. A process according to claim 21, wherein said capsid proteins are allowed to self-associate to form capsid structures.

23. A process for preparing the yeast-Ty particle of claim 2, wherein said process comprises the steps:

(a) expressing in yeast cells, a DNA coding for TyA protein, which contains a membrane-active peptide at the carboxy terminus;

(b) opening up the yeast cells of step (a); and (c) harvesting the yeast-Ty particle therefrom.

24. A process for preparing the MS2 particle of claim 5, wherein said process comprises the steps:

(a) expressing a DNA coding for the MS2 capsid protein which contains a sequence inserted therein coding for a membrane-active peptide, thereby obtaining a modified capsid protein;

(b) denaturing the modified capsid protein of step (a) with a denaturing agent;

(c) removing the denaturing agent of step (b); and (d) allowing the modified capsid protein to associate.

* * * * *

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 34 Base pairs
        ( B ) TYPE: Nucleic acid
        ( C ) STRANDEDNESS: Single stranded
        ( D ) TOPOLOGY: linear ( i i ) MOLECULE TYPE: synthetic oligodeoxyribonucleotide ( x i ) SEQUENCE DESCRIPTION: SEQ ID NO: 1:

GACCCAAAAC CAAGCCAATC CATCTGGTTG GTCA      34

( 2 ) INFORMATION FOR SEQ ID NO: 2:

( i ) SEQUENCE CHARACTERISTICS:
        ( A ) LENGTH: 33 Base pairs
        ( B ) TYPE: Nucleic acid
        ( C ) STRANDEDNESS: Single stranded
        ( D ) TOPOLOGY: linear ( i i ) MOLECULE TYPE: synthetic oligodeoxyribonuceotide ( x i ) SEQUENCE DESCRIPTION: SEQ ID NO: 2:

TGTAACTGGA TCCCCTTTGG GTTTGGTTGT ATT      33

( 2 ) INFORMATION FOR SEQ ID NO: 3:

( i ) SEQUENCE CHARACTERISTICS:
        ( A ) LENGTH: 35 Base pairs
        ( B ) TYPE: Nucleic acid
        ( C ) STRANDEDNESS: Single stranded
        ( D ) TOPOLOGY: linear ( i i ) MOLECULE TYPE: synthetic oligodeoxyribonucleotide ( x i ) SEQUENCE DESCRIPTION: SEQ ID NO: 3:

GGTACCTGGA TCCCGTTATA GCTCGGAATC CTCAA      35

( 2 ) INFORMATION FOR SEQ ID NO: 4:

( i ) SEQUENCE CHARACTERISTICS:
        ( A ) LENGTH: 25 Base pairs
        ( B ) TYPE: Nucleic acid
        ( C ) STRANDEDNESS: Single stranded
        ( D ) TOPOLOGY: linear ( i i ) MOLECULE TYPE: synthetic oligodeoxyribonucleotide ( x i ) SEQUENCE DESCRIPTION: SEQ ID NO: 4:

TCAAGGGCAT CGGTCGACGC TCTCC      25

( 2 ) INFORMATION FOR SEQ ID NO: 5:

( i ) SEQUENCE CHARACTERISTICS:
        ( A ) LENGTH: 18 Base pairs
        ( B ) TYPE: Nucleic acid
        ( C ) STRANDEDNESS: Single stranded
        ( D ) TOPOLOGY: linear ( i i ) MOLECULE TYPE: synthetic oligodeoxyribonucleotide ( x i ) SEQUENCE DESCRIPTION: SEQ ID NO: 5:

GATCCTAAAT TGAATTGA 18

( 2 ) INFORMATION FOR SEQ ID NO: 6:

( i ) SEQUENCE CHARACTERISTICS:
        ( A ) LENGTH: 18 Base pairs
        ( B ) TYPE: Nucleic acid
        ( C ) STRANDEDNESS: Single stranded
        ( D ) TOPOLOGY: linear ( i i ) MOLECULE TYPE: synthetic oligodeoxyribonucleotide ( x i ) SEQUENCE DESCRIPTION: SEQ ID NO: 6:

GATCTCAATT CAATTTAG 18

( 2 ) INFORMATION FOR SEQ ID NO: 7:

( i ) SEQUENCE CHARACTERISTICS:
        ( A ) LENGTH: 93 Base pairs
        ( B ) TYPE: Nucleic acid
        ( C ) STRANDEDNESS: Single stranded
        ( D ) TOPOLOGY: linear ( i i ) MOLECULE TYPE: synthetic oligodeoxyribonucleotide ( i i i ) ANTI-SENSE: NO ( i x ) FEATURE:
        ( A ) NAME/KEY: CDS
        ( B ) LOCATION: 7..93

( x i ) SEQUENCE DESCRIPTION: SEQ ID NO: 7:

```
GATCTA GAA GCC GCC TTG GCC GAA GCC TTG GCC GAA GCC TTG GCC GAA      48
       Glu Ala Ala Leu Ala Glu Ala Leu Ala Glu Ala Leu Ala Glu
       1               5                  10

CAC TTG GCC GAA GCC TTG GCC GAA GCC TTG GAA GCC TTG GCC GCC         93
His Leu Ala Glu Ala Leu Ala Glu Ala Leu Glu Ala Leu Ala Ala
15                  20                  25
```

( 2 ) INFORMATION FOR SEQ ID NO: 8:

( i ) SEQUENCE CHARACTERISTICS:
        ( A ) LENGTH: 29 Amino acids
        ( B ) TYPE: Amino acid
        ( D ) TOPOLOGY: linear ( i i ) MOLECULE TYPE: Protein ( x i ) SEQUENCE DESCRIPTION: SEQ ID NO: 8:

```
Glu Ala Ala Leu Ala Glu Ala Leu Ala Glu Ala Leu Ala Glu His Leu
1               5                  10                  15

Ala Glu Ala Leu Ala Glu Ala Leu Glu Ala Leu Ala Ala
                20                  25
```

( 2 ) INFORMATION FOR SEQ ID NO: 9:

( i ) SEQUENCE CHARACTERISTICS:
        ( A ) LENGTH: 93 Base pairs
        ( B ) TYPE: Nucleic acid
        ( C ) STRANDEDNESS: Single stranded
        ( D ) TOPOLOGY: linear ( i i ) MOLECULE TYPE: synthetic oligodeoxyribonucleotide ( i i i ) ANTI-SENSE: YES ( x i ) SEQUENCE DESCRIPTION: SEQ ID NO: 9:

GATCTGGCGG CCAAGGCTTC CAAGGCTTCG GCCAAGGCTT CGGCCAAGTG TTCGGCCAAG 60

GCTTCGGCCA AGGCTTCGGC CAAGGCGGCT TCT 93

( 2 ) INFORMATION FOR SEQ ID NO: 10:

( i ) SEQUENCE CHARACTERISTICS:
        ( A ) LENGTH: 106 Base pairs
        ( B ) TYPE: Nucleic acid
        ( C ) STRANDEDNESS: Single stranded
        ( D ) TOPOLOGY: linear ( i i ) MOLECULE TYPE: synthetic oligodeoxyribonucleotide ( i i i ) ANTI-SENSE: NO ( i x ) FEATURE:
        ( A ) NAME/KEY: CDS
        ( B ) LOCATION: 7..105

( x i ) SEQUENCE DESCRIPTION: SEQ ID NO: 10:

```
GATCTA GGT TTG TTC GAA GCC ATT GAA GGT TTC ATT GAA AAC GGT TGG         48
       Gly Leu Phe Glu Ala Ile Glu Gly Phe Ile Glu Asn Gly Trp
        1               5                      10

GAA GGT TTG GCC GAA GCC TTG GCC GAA GCC TTG GAA GCC TTG GCC GCC         96
Glu Gly Leu Ala Glu Ala Leu Ala Glu Ala Leu Glu Ala Leu Ala Ala
 15              20              25                  30

GGT GGT TCT A                                                          106
Gly Gly Ser
```

( 2 ) INFORMATION FOR SEQ ID NO: 11:

( i ) SEQUENCE CHARACTERISTICS:
        ( A ) LENGTH: 33 Amino acids
        ( B ) TYPE: Amino acid
        ( D ) TOPOLOGY: linear ( i i ) MOLECULE TYPE: Protein ( x i ) SEQUENCE DESCRIPTION: SEQ ID NO: 11:

```
Gly Leu Phe Glu Ala Ile Glu Gly Phe Ile Glu Asn Gly Trp Glu Gly
 1               5                  10                  15

Leu Ala Glu Ala Leu Ala Glu Ala Leu Glu Ala Leu Ala Ala Gly Gly
             20                  25                  30

Ser
```

( 2 ) INFORMATION FOR SEQ ID NO: 12:

( i ) SEQUENCE CHARACTERISTICS:
        ( A ) LENGTH: 105 Base pairs
        ( B ) TYPE: Nucleic acid
        ( C ) STRANDEDNESS: Single stranded
        ( D ) TOPOLOGY: linear ( i i ) MOLECULE TYPE: synthetic oligodeoxyribonucleotide ( i i i ) ANTI-SENSE: YES ( i x ) FEATURE:
        ( A ) NAME/KEY: misc_feature
        ( B ) LOCATION: 1..105

( x i ) SEQUENCE DESCRIPTION: SEQ ID NO: 12:

```
GATCTAGAAC CACCGGCGGC CAAGGCTTCC AAGGCTTCGG CCAAGGCTTC GGCCAAACCT    60

TCCCAACCGT TTTCAATGAA ACCTTCAAGG CTTCGAACAA ACCTA                  105
```

( 2 ) INFORMATION FOR SEQ ID NO: 13:

( i ) SEQUENCE CHARACTERISTICS:
        ( A ) LENGTH: 32 Base pairs
        ( B ) TYPE: Nucleic acid -continued

```
        ( C ) STRANDEDNESS: Single stranded
        ( D ) TOPOLOGY: linear ( i i ) MOLECULE TYPE: synthetic oligodeoxyribonucleotide ( i i i ) ANTI-SENSE: NO ( i x ) FEATURE:
            ( A ) NAME/KEY: CDS
            ( B ) LOCATION: 2..31

( x i ) SEQUENCE DESCRIPTION: SEQ ID NO: 13:

T ATG GCT AGC CAC CAT CAC CAT CAC CAT GGT G                               3 2
  Met Ala Ser His His His His His His Gly
   1               5                  10

( 2 ) INFORMATION FOR SEQ ID NO: 14:

( i ) SEQUENCE CHARACTERISTICS:
            ( A ) LENGTH: 10 Amino acids
            ( B ) TYPE: Amino acid
            ( D ) TOPOLOGY: linear ( i i ) MOLECULE TYPE: Protein ( x i ) SEQUENCE DESCRIPTION: SEQ ID NO: 14:

Met Ala Ser His His His His His His Gly
 1               5                  10

( 2 ) INFORMATION FOR SEQ ID NO: 15:

( i ) SEQUENCE CHARACTERISTICS:
            ( A ) LENGTH: 34 Base pairs
            ( B ) TYPE: Nucleic acid
            ( C ) STRANDEDNESS: Single stranded
            ( D ) TOPOLOGY: linear ( i i ) MOLECULE TYPE: synthetic oligodeoxyribonucleotide ( i i i ) ANTI-SENSE: YES ( i x ) FEATURE:
            ( A ) NAME/KEY: misc_feature
            ( B ) LOCATION: 1..34

( x i ) SEQUENCE DESCRIPTION: SEQ ID NO: 15:

GATCCACCAT GGTGATGGTG ATGGTGGCTA GCCA                                     3 4
```